United States Patent [19]
Scholz et al.

[11] Patent Number: 5,803,086
[45] Date of Patent: Sep. 8, 1998

[54] LINERLESS SURGICAL INCISE DRAPE

[75] Inventors: Matthew T. Scholz, Woodbury, Minn.; Andrew J. Stockholm, Brookings, S. Dak.; Kristen L. Comstock, Minneapolis; John E. Bruno, Lindstrom, both of Minn.; Dietmar Schlei, Hudson, Wis.

[73] Assignee: Minnesota Mining and Manufacturing Company, St. Paul, Minn.

[21] Appl. No.: 759,244

[22] Filed: Dec. 2, 1996

Related U.S. Application Data

[63] Continuation-in-part of Ser. No. 724,744, Oct. 2, 1996, abandoned, which is a continuation-in-part of Ser. No. 648,903, May 16, 1996, abandoned.

[51] Int. Cl.$^6$ .................................................. A61B 19/00
[52] U.S. Cl. ............................................ 128/849; 128/851
[58] Field of Search ................................... 128/849–856

[56] References Cited

U.S. PATENT DOCUMENTS

| | | | |
|---|---|---|---|
| Re. 31,886 | 5/1985 | Hodgson | 428/40 |
| Re. 31,887 | 5/1985 | Hodgson | 428/355 |
| 3,060,932 | 10/1962 | Pereny | 128/849 |
| 3,349,765 | 10/1967 | Blanford | 128/851 |
| 3,916,887 | 11/1975 | Kelly | 128/851 |
| 4,310,509 | 1/1982 | Berglund et al. | 424/28 |
| 4,323,557 | 4/1982 | Rosso et al. | 424/28 |
| 4,374,520 | 2/1983 | Grossmann et al. | 128/132 |
| 4,452,845 | 6/1984 | Lloyd et al. | 428/220 |
| 4,570,627 | 2/1986 | MacConkey et al. | 128/132 D |
| 4,701,509 | 10/1987 | Sun et al. | 526/264 |
| 4,732,808 | 3/1988 | Krampe et al. | 428/355 |
| 4,798,201 | 1/1989 | Rawlings et al. | 128/156 |
| 4,931,282 | 6/1990 | Asmus et al. | 424/448 |
| 5,017,625 | 5/1991 | Ansell | 521/159 |
| 5,038,798 | 8/1991 | Dowdy et al. | 128/853 |
| 5,156,911 | 10/1992 | Stewart | 428/355 |
| 5,197,493 | 3/1993 | Grier-Idris | 128/849 |
| 5,204,110 | 4/1993 | Cartmell et al. | 424/443 |
| 5,290,615 | 3/1994 | Tushaus et al. | 428/40 |
| 5,480,377 | 1/1996 | Cartmell et al. | 602/48 |
| 5,586,563 | 12/1996 | Newman | 128/853 |

OTHER PUBLICATIONS

Karen S. Hagen et al., "A Comparison of Two Skin Preps Used in Cardiac Surgical Procedures," *Aorn Journal*, 62, 393–402 (1995).

*Primary Examiner*—Michael A. Brown
*Attorney, Agent, or Firm*—Robert W. Sprague

[57] ABSTRACT

A linerless, easy to apply surgical incise drape including a flexible film which has one major surface coated with a pressure sensitive adhesive and of the opposite major surface coated with a low adhesion backsize. The drape is rolled around a cylindrical core. The drape of the invention eliminates the need to use a separate liner to protect the adhesive surface of the drape, reducing the cost of the drape and eliminating waste.

24 Claims, 3 Drawing Sheets

LINERLESS SURGICAL INCISE DRAPE

CROSS REFERENCE TO RELATED APPLICATION

This application is a continuation-in-part of application Ser. No. 08/724,744 filed Oct. 2, 1996, now abandoned, which is a continuation-in-part of application Ser. No. 08/648,903 filed May 16, 1996, now abandoned.

FIELD OF THE INVENTION

The present invention relates to an incise drape suitable for use in surgical procedures. More specifically, the linerless incise drape includes a pressure-sensitive adhesive (PSA) coating on one side of a polymeric film, with a low adhesion backsize (LAB) coating on the opposite side of the film. Such a construction allows the drape to be rolled around a core for easy delivery. Thus, the incise drapes of this invention have significantly lower raw material cost, and far less waste is generated by eliminating the use of the liner.

BACKGROUND OF THE INVENTION

Many of today's surgical procedures involve the use of an incise drape. The incise material is usually a clear polymeric film with an adhesive on one side which is in turn covered with a release liner. Two suppliers of incise material are the Minnesota Mining and Manufacturing Company and T. J. Smith and Nephew Ltd. Examples of incise material can be found, by way of example only, in U.S. Pat. Nos. 4,310,509; 4,323,557; 4,452,845; Re. 31,886 and Re. 31,887. Most typically incise material is used in connection with towels or surgical drapes to maintain the surgical area as clean and sterile as possible to help reduce the risk of surgical site infection. Once the surgical area of the patient has been scrubbed and treated with an antimicrobial, the surgical site is squared-off by the use of sterile towels and a surgical drape which has a fenestration of a size which is larger than the expected size of the incision. An incise material is then used to cover all or a portion of the patient's skin left exposed by the towels or the fenestration in the surgical drape or mainsheet. One purpose in using the incise material is to help reduce the migration of germs and bacteria into the incision site. This is because, despite the cleansing of the skin, the pores still contain additional germs and bacteria which can migrate to the surface as the skin is moved and worked during the course of the surgical procedure. By covering the skin with incise material, it has been found that a lower incidence of surgical site infection occurs.

Common practice is to take the folded sterile incise drape out of a disposable, protective bag (e.g., made from polyethylene) and deliver it to the sterile field in an aseptic manner. The drape typically comes in sizes as small as 13×18 cm (5×7 inches) up through 90×120 cm (36×48 inches) and larger. Conventional surgical drapes usually consist of an antimicrobial film incise material covered by a single sheet of silicone coated paper release liner with dimensions equal to the film so that the adhesive is protected. Typical practice is for two people to stand on opposite sides of the operating table, each within the sterile field with sterile gloved hands. One person grips the handle portion of the drape (a 10 to 15 cm (4 to 6 inches) film margin free of adhesive) while the other person takes the paper liner and pulls it away from the underside exposing the adhesive and unfolding the drape. The drape is then applied to the patient at the surgical site and subsequently smoothed out and pressed onto the patient with a sterile towel. The liner portion must be removed properly to avoid contamination of the drape or patient and then must be properly disposed.

Occasionally, during the application process the release liner may tear, complicating delivery and sometimes wrinkling the drape and rendering it useless. Furthermore, in addition to the added expense caused by the use and disposal of the liner, the liner may introduce debris to the sterile field, to the detriment of the patient.

Current incise drapes are usually large and cumbersome to unfold and apply to the patient without wrinkles and without the drape sticking to itself in the process. Applying conventional incise drapes can be a frustrating experience, even for those skilled in the art of applying incise drapes. The drape is flimsy (so as to be very conformable to the contours of the skin) with an aggressive pressure sensitive adhesive for adhesion to the skin. These two quality characteristics, when combined with the large size of incise drapes, frequently result in the application of a wrinkled drape.

It is imperative that the incise drape be wrinkle-free after it is applied, especially directly at the incision point in order for the surgeon to be able to make a clean surgical incision. Wrinkles in the drape make it difficult for the surgeon to see through to the skin (translucency and visibility are important) and, more importantly, wrinkles may not contain the bacteria on the skin as well as a smooth drape. It is of utmost importance to maintain a sterile surface at the point of incision in order to prevent a possible surgical wound infection, which could lead to serious bacterial infections and, which may even be fatal. Such infections can be very expensive to treat, costing the hospital tens of thousands of dollars. Hager, K. S.; Treston-Aurand, J. "A Comparison of Two Skin Preps Used in Cardiac Surgical Procedures," AORN Journal, Vol. 62, No. 3, September 1995.

Clearly a need exists for an incise drape that can be effectively applied to the patient in wrinkle-free form so as to minimize the chance of infection and improve the visibility through the film.

SUMMARY OF THE INVENTION

The present invention relates to lower cost and easier to apply adhesive coated incise drapes useful in surgical procedures. The incise drapes of this invention differ considerably from those in the prior art by having essentially no liner. The incise drapes of this invention comprise a flexible film backing coated on one side with a dermatologically acceptable pressure sensitive adhesive (PSA) and on the opposite side with a low adhesion backsize (LAB). In a preferred embodiment, at least two of the opposite edges of the drape have "handles" attached which are not coated with adhesive and serve to facilitate application and removal of the drape. At least one of the handles serves as a core on which the drape is subsequently wound. The handle may be comprised of a circular core (e.g., cardboard or plastic) but is preferably a wound up section of low adhesion sheet material. In this manner, the incise drape can be applied by two people wherein one person holds the core (e.g., with a finger or rod inserted in either end of the core or in embodiments where the core extends beyond the adhesive coated film the core may be held on the outside of the protruding ends) and a second person unrolls the drape by pulling on the handle protruding from the opposite end of the drape on the outside of the roll.

Applicants have discovered that the incise drapes of this invention which are presented in rolled form 1) eliminate the need to use a separate liner to protect the adhesive portion of the drape, reducing the cost of the drape and eliminating waste; 2) reduce the amount of drape wrinkling that occurs during application; and 3) improve ease of drape application.

BRIEF DESCRIPTION OF THE DRAWINGS

Reference may be made to the drawings which illustrate preferred embodiments of the invention with like reference numerals referring to like parts and in which.

DETAILED DESCRIPTION OF PREFERRED EMBODIMENTS

Figure 1:
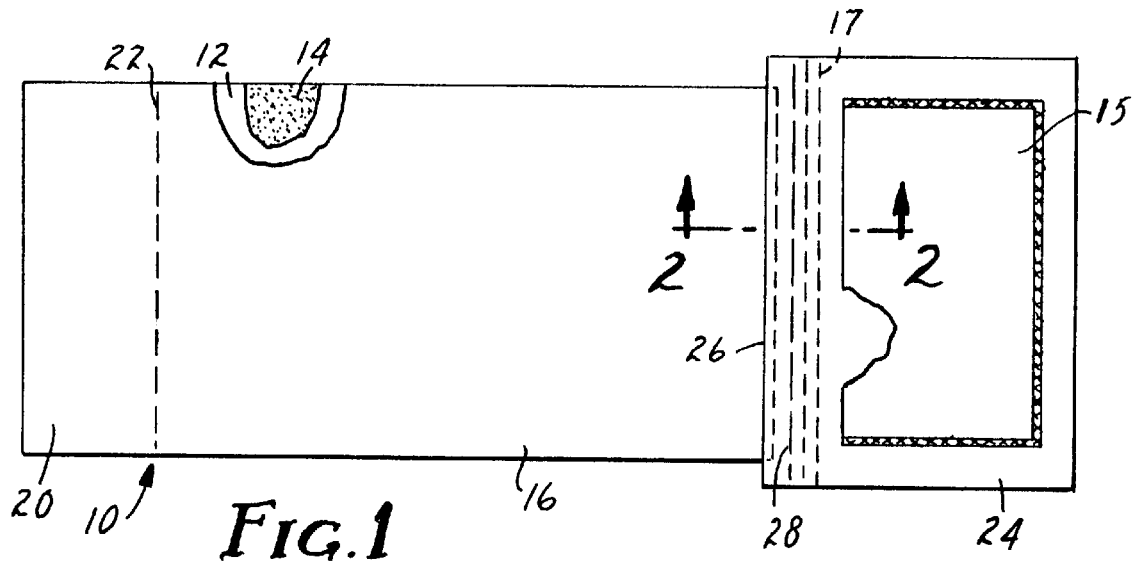
FIG. 1 is a plan view of an embodiment of the present invention, parts thereof broken away to illustrate various layers.
Figure 2:
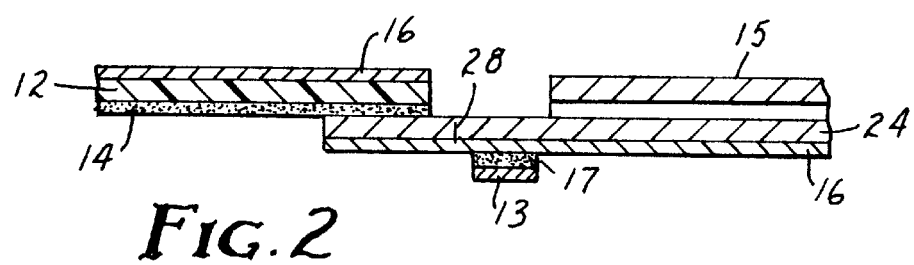
FIG. 2 is an enlarged sectional view taken along the line 2—2 of FIG. 1, not to scale.
Figure 3:
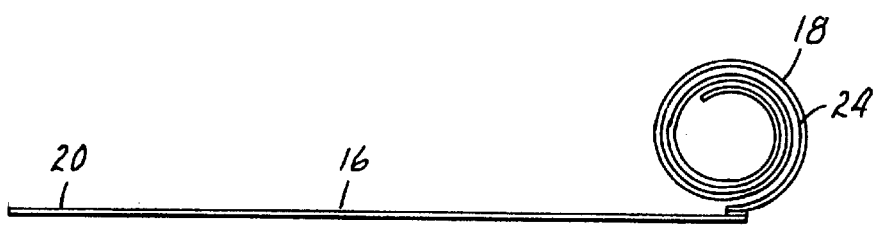
FIG. 3 is a side view of an alternative embodiment of the present invention, partially rolled.
Figure 4:
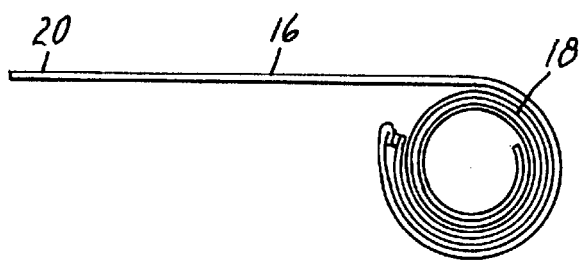
FIG. 4 is a side view of the embodiment illustrated in FIG. 3, further rolled.

FIG. 1 illustrates the linerless surgical incise drape 10 of this invention, in the unrolled state. Referring to FIG. 2, the drape 10 is constructed of a film backing 12 on one side of which is coated a pressure sensitive adhesive 14. On the opposite side of film backing 12 is coated a low adhesion backsize (LAB), 16. As shown in FIGS. 3 and 4, the drape is rolled adhesive surface inward around a cylindrical core 18 with a handle 20 extending from the terminal end of the roll. The handle 20 consists of a non-adhesive coated portion which may be simply the film backing 12 extending beyond the adhesive coated portion 14 or may be a second material bonded to edge 22 of film backing 12. Though not illustrated, drape 10 may alternatively be rolled adhesive surface outward. In such event, handle 20 preferably includes a low adhesion backsize on the adhesive contacting surface such that when the drape is wound up, the handle 20 is wrapped around the exterior surface thereby covering the portion of pressure sensitive adhesive which would otherwise be exposed.

Referring to FIGS. 1 and 4, the handle 20 serves to allow for easy application of the rolled drape by providing a means to unwind the roll. In a preferred embodiment the handle is stiff relative to film backing 12 and serves to reduce wrinkling of the drape as it is unwound. The handle 20 also facilitates removal of the incise drape from the patient once the surgery is complete. Still further, handle 20 may extend beyond the roll itself and, provided it comprises a relatively stiff material, handle 20 can thereby prevent the roll from rolling off a sterile field where it has been placed. Finally, handle 20 can have printed thereon instructions for using and information concerning the drape. Handle 20 may be permanently attached to the adhesive coated drape or it may be removable by use of a removable adhesive attachment, a perforation, or similar means. The core 18 may be, for example, constructed of a piece of low adhesion sheet material 24 attached to drape 10 at edge 26, opposite handle 20.

Figure 6:
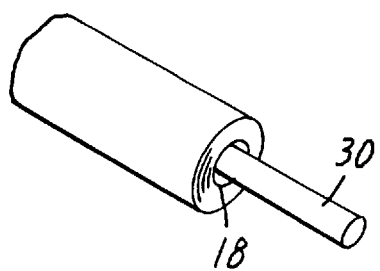
FIG. 6 is a partial perspective view of the drape of FIG. 1, with inclusion of a rod.

Sheet material 24 is rolled up as shown in FIGS. 3 and 4 to form the core 18 which, after application, can remain attached to the drape to serve as a second handle for easy removal of the drape post surgery. Alternatively, a separate cylindrical core may be used. In either case, core 18 preferably extends beyond the edge of the adhesive coated drape. In this manner, the protruding ends of the core may be application handles lightly held by an applier as the drape is unwound during application. Each of these core handles preferable extend at least 2 cm and more preferably at least 3 cm beyond the adhesive coated drape. Alternatively, a rod 30 may be inserted into the core 18 to facilitate application, as shown in FIG. 6. In yet another embodiment, if the core diameter is large enough, the fingers of one of the persons applying the drape may be inserted into opposite ends of the core 18.

Sheet material 24 forming the core 18 may be permanently attached to the drape 10 or may be releasably attached by means of an adhesive or use of a perforation 28, as shown in FIG. 1.

In a preferred embodiment as shown in FIGS. 3 and 4, the sheet material 24 is wound in reverse direction from the drape 10. Applicants have found that when sheet 24 is wound in the same direction as drape 10, as the drape is being unwound for application, the wound sheet 24 tightens around the rod or fingers of the applier, prohibiting further unrolling. This tightening is referred to as "neck down." However, winding of the sheet 24 in the opposite direction from the drape, neck down is eliminated. Alternatively or additionally, it is helpful to flatten core 18 after winding, or tack the wound sheet material 24 to itself, to prevent neck down.

Figure 5:
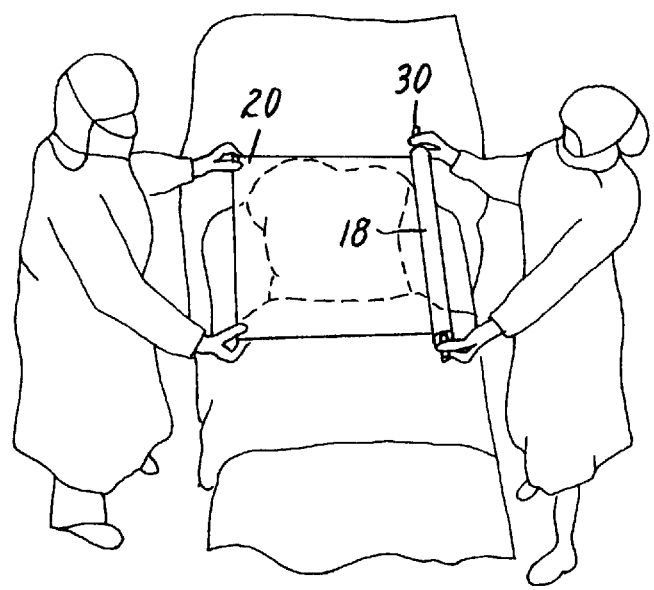
FIG. 5 is a perspective view showing application of the drape to a patient.

As illustrated in FIGS. 5 and 6, the linerless incise drape of FIG. 5 is grasped at handle 20 by the sterile gloved hand of one health care worker, while another health care worker holds the core 18, for example, at rod 30. Typically, a portion of the drape is unrolled from the core 18 (preferably unrolled by about ⅔ the length of the drape), and applied adhesive 14 side down to the patient at the incision site. Unrolling of the drape is continued with application to the patient. Alternatively, the drape may be applied to the patient as it is unwound. In this case, it is particularly advantageous to have the drape rolled adhesive side out which facilitates unrolling the drape as it is applied to the patient. These methods of delivery yield a very smooth, wrinkle-free drape. For application to certain body parts, such as an extremity, the roll delivery of this invention allows the clinician to wrap the drape in an overlapping fashion such as a spiral wind. This significantly reduces the amount of wrinkles during application.

The sheet material 24 forming the core 18 may be a paper liner, plastic, or composite laminate liner coated on one side with a premium release coating such as the low adhesion backsize (LAB) coatings described below. In order to serve as a core, it is important that the sheet 24 have sufficient stiffness to support unwinding the drape. Paper materials preferably have a basis weight of at least 100 g/m² and more preferably of at least 150 g/m² and have thicknesses of greater than about 4 mil (0.1 mm). Plastic sheets may be comprised of polyolefins, polyesters, polyurethanes and polyamides but are preferably polyolefins such as polyethylene or polypropylene or polyesters such as polyethylene terephthalate. Plastic sheets are preferably at least 2 mil (0.05 mm) thick. It is also possible to use a conventional cylindrical core comprised of cardboard, paperboard, plastic and the like. When using a conventional core, the core is preferably easily detachable from the incise drape after application. The core will typically have a diameter of less than 4.0 cm and preferably less than about 2.5 cm. The core may be removed post application by a variety of means including providing a perforation in the drape or alternatively using a core to which the drape is releasably attached. The drape may be releasably attached to the core either by application of a release coating to the core or by using a core with an inherently low surface energy that allows detachment, e.g., a polyolefin or fluorinated polyolefin. In embodiments where the drape is releasably attached to the core, the force required to remove the drape from the core is preferably at least 15%, more preferably at least 25%, and most preferably at least 40% greater than the force required to unwind the roll. In this manner, the roll can be unwound until it reaches a natural "stop" at the core, thus preventing the clinician from losing control of the drape. Without this differential unwind tension the drape might otherwise completely unroll, fall of the core, and wrinkle. Once the drape is applied, the core can be removed by pulling the core with the greater force required to releasably detach the drape.

Referring to FIGS. 1 and 2, when core 18 is formed by rolling up a section of sheet material 24, it is optionally releasably attached to film 12 preferably using a perforation 28. Other methods of releasably attaching sheet material 24, such as adhesive and thermal bonds, may be used. In a further embodiment of the present invention sheet material 24 and/or handle 20 may optionally include a pouch 15 (or multiple pouches). Alternatively, or in addition, the sheet material 24 may include other attachments such as tubing organizers, cautery holsters, instrument holders, fluid collection pouches, etc. The pouch 15 may be formed by sealing a piece of plastic film, paper, or other textile cloth, including wovens, knits and non-wovens, or laminates thereof, to the surface of the sheet material 24. Preferably, a thermoplastic film is used. Sealing means include transfer adhesive, hot melt adhesive, double coated tape, heat sealing, ultrasonic sealing and the like. Preferably, the pouches are formed by heat sealing a thermoplastic film directly to the sheet material 24. The three major edges of the pouch define an opening, which for larger pouches may be used as a fluid collection means, and, for smaller pouches, may be used for storage of the surgical supplies and instruments. The opening of the pouch so formed may further have a means of keeping the pouch "open" so that the fluid may drain into the pouch. For example, a piece of reticulated foam may be used. Furthermore, the edge of the pouch defining the opening may be formed by folding the film back on itself providing reinforcement to the opening.

Additionally, when sheet material 24 is removed, it may further be used to cover other areas on the patient, instruments, etc., by reattachment using adhesive section 17. Ordinarily, adhesive section 17 is protected by a piece of release liner 13, as is known in the art.

The film 12 of the incise drape is formed from a substantially transparent or translucent flexible polymeric material which preferably allows for moisture evaporation through the film during prolonged surgeries. Suitable materials include polyolefins, such as low density polyethylene, polyurethanes such as polyester or polyether polyurethanes, (e.g., "Estane® Thermoplastic Polyurethane," commercially available from B.F. Goodrich, Cleveland, Ohio), polyesters such as polyether polyester (e.g., "Hytrel® polyester elastomer," commercially available from Du Pont Co., Wilmington, Del.), and polyamides such as polyether polyamides (e.g., "Pebax® Resins" commercially available from ELF Atochem, North America, Inc., Philadelphia, Pa.). Furthermore, the film is preferably somewhat elastomeric to improve conformability. For these reasons, the preferred films are polyurethanes, polyether polyesters, and polyether polyamides. The film will typically have a thickness of less than 200 microns, preferably between about 6 to 130 microns, and most preferably between about 13 and 52 microns.

The adhesive on the film is preferably a tacky pressure sensitive adhesive at room temperature which will adhere aggressively to the skin. Good attachment to the skin surface is critical to maintain a sterile surgical field. Aggressive adhesives are preferred due to the stress the incise drape is under during surgery as a result of the retraction of the wound, the warm moist environment, and the abrasion the drape may encounter at the surgeon's hands as instruments move in and out of the wound. Suitable adhesives include acrylic adhesives, rubber based adhesives such as those based on natural rubber, polyisobutylene, butylene rubbers and the like, polyurethane type adhesives, and polyvinylethyl ether and copolymers or blends of these. Preferably the adhesive also contains an antimicrobial such as iodine, triiodide complexes, lactam-triiodide complexes such as povidone-iodine, chlorhexidine salts such as chlorhexidine gluconate and chlorhexidine acetate, hexachlorophene, parachlorometaxylenol (PCMX, phenols, Lauricidin (glycerol monolaurate), quaternary surfactants, silver, and silver salts such as silver chloride, silver oxide and silver, hydrogen peroxide and the like. The adhesive is preferably one of those described in U.S. Pat. Nos. 4,323,557; 4,931,282; 4,701,509; 4,732,808; 5,156,911; 5,017,625; and 5,204,110, incorporated herein by reference. It will be appreciated by one skilled in the art that the aforestated adhesive types might also include various chemical modifiers e.g., tackifiers, crosslinkers, stabilizers, initiators, etc. to improve physical properties such as stability, viscosity, adhesion and the like. The adhesive may be a continuous coating or may be pattern coated as described in U.S. Pat. Nos. 4,798,201 and 5,290,615, incorporated herein by reference. Preferably the adhesive is coated over at least 50 percent of the area of the film backing 12, more preferably 80 percent, still more preferably 90 percent, and most preferably 100 percent.

Figure 7:
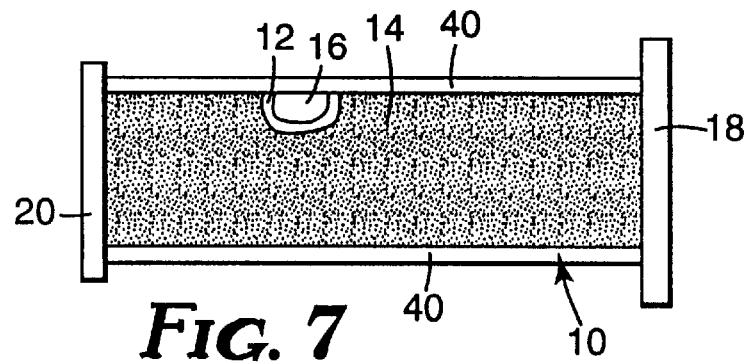
FIG. 7 is a plan view of an alternative embodiment of the present invention.
Figure 8:
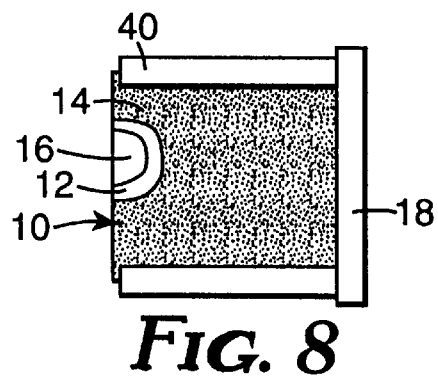
FIG. 8 is a plan view of an alternative embodiment of the present invention.
Figure 9:
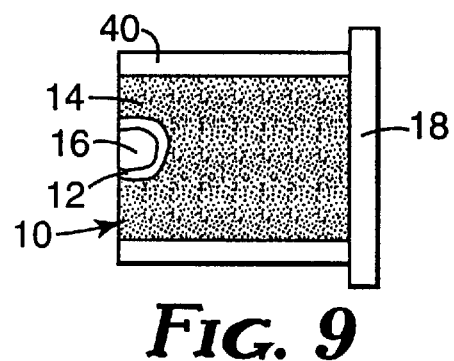
FIG. 9 is a plan view of an alternative embodiment of the present invention.

As stated previously, film 12 is preferably very thin and conformable and adhesive 14 is very aggressive in order to adhere tenaciously to the skin. This combination of a "flimsy" film and aggressive adhesive has been found to typically result in adherence of adjacent layers in the rolled product at the edges of the roll whether the drape is rolled adhesive surface inward or outward relative to the core. Once adjacent layers adhere, unrolling can be difficult, if not impossible, sometimes even resulting in forces sufficient to rip the drape. For this reason, it has been found advantageous to treat the edges of the incise drape in order to prevent edge adhesion in the rolled product. For example, it has proven useful to apply a fine particulate to the outer edge which blinds the adhesive thus preventing edge adhesion. It has been found advantageous to apply the particulate material prior to converting into roll form. In this manner, the extreme outer 0.1–1.0 cm edge may be detackified by application of the particulate. Any finely divided solid may work to detackify the edge including organic and inorganic powders, dusts, bubbles, and the like. Examples of the particulate include silica, glass bubbles, clays, talc, polymeric micropowders and the like. When using the powder type materials, care must be taken to ensure non-adhered residual particulate does not contaminate the rest of the drape such that it could be deposited on the outer surface or in the wound created by the surgical incision. Alternatively, a narrow width non-adhesive coated strip (40) may be applied to the outer edge of the incise drape as shown in FIG. 7 by means of pressure sensitive adhesive 14. This strip may extend beyond the outer edge of the adhesive coated drape 10 as shown in FIG. 8 or may be adhered right to the edge (or slightly indented to the edge) as shown in FIG. 9. In this manner, the strip serves to ensure that edge adhesion cannot occur. Use of a strip offers manufacturing advantages since the strip may be applied continuously as the product is coated or may be applied immediately prior or immediately after a slitting operation. The strip preferably is about less than about 4 cm wide, more preferably less than 2 cm wide, and most preferably less than about 1.5 cm wide. In certain embodiments, such as where either or both the handle and core have been removed, the edge strips 40 may provide a means to grasp the drape thereby facilitating removal. In these embodiments the edge strips may be as much as 5 to 7.5 cm wide or wider. The thickness of the strip is controlled to ensure that it does not detrimentally affect the conformability of the drape and may actually help to prevent wrinkling of these edges during application. Therefore, the strip is preferably about 10–100 micron thick and more preferably 20–80 micron thick. The strip may be paper or a polymeric film or non-woven. Films and non-wovens are comprised of relatively tough thermoplastic or thermoset materials but are preferably thermoplastics such as polyolefins, vinylic copolymers such as ethylene vinylacetate, polyvinylacetate/alcohol, ethyleneacrylate copolymers (e.g., ethylenemethacrylate, EMAC™ and ethylene/butylacrylate, EBAC™ products of Chevron Chemical Company, Specialty Polymers Group, Houston, Tex.) polyesters, polyurethanes, polyamides, and the like including laminates of these materials. Cast or blown films may be used. Non-woven produced from non-thermoplastic fibers such as rayon, cotton, and other natural fibers may also be suitable. Paper strips include any of the papers known including papers coated with binders and release coatings as well as paper/film laminates. Preferred strips are low cost films of polyethylene or polyester. Also preferred are relatively non-extensible materials such as polyolefins which facilitate application of the drape by a procedure involving unrolling the drape prior to application to the body. A non-extensible material as strip 40 reduces unwanted extension of the drape during the unrolling and application thereof.

Figure 10:
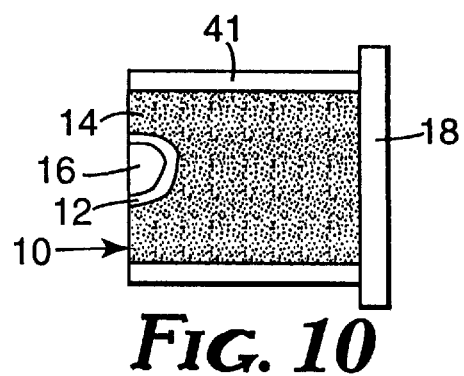
FIG. 10 is a plan view of an alternative embodiment of the present invention.

A further alternative to ensure no significant edge adhesion in the rolled product is to "zone" coat film 12 with adhesive 14 leaving zone 41 of non-coated film 14 at the outer edge as shown in FIG. 10. This coating may be accomplished by in some manner blocking the coating die or may be accomplished by coating the film 12 with an overlay strip which is subsequently removed after coating to leave the uncoated portion 41. These uncoated outer edges may also serve to facilitate removal of the drape similar to edge strips 40.

We claim:

1. A surgical incise drape comprising a substantially transparent flexible film which has at least a major portion of one major surface coated with a pressure sensitive adhesive and at least a major portion of the opposite major surface coated with a low adhesion backsize, wherein the drape is rolled around a core so that the surface coated with the pressure sensitive adhesive releasably engages with the low adhesion backsize surface.

2. The surgical incise drape of claim 1 wherein a non-adhesive coated handle portion extends from the film at its terminal end.

3. A method of applying the surgical drape of claim 2 to a patient comprising the steps of
   a) a first health care worker grasping the handle of the drape, while a second health care worker holds the core in such a manner that the core may rotate;
   b) the first health care worker pulling on the handle so as to unroll a portion of the film;
   c) the first health care worker applying the adhesive surface of the film to the desired position on the patient; and
   d) the health care workers continuing to unroll the film from the core while the newly exposed adhesive surface of the film is applied to the patient.

4. The surgical incise drape of claim 1 wherein the core comprises a rolled piece of low adhesion sheet material.

5. The surgical drape of claim 4 wherein the sheet material of the core is rolled in the reverse direction from the film drape.

6. The surgical drape of claim 4 wherein the rolled sheet material is flattened or tacked to itself.

7. The surgical drape of claim 4 wherein the sheet material is removably attached to the end of the film which is first wound around the core.

8. The surgical drape of claim 7 wherein the sheet material has at least one adhesive portion which allows the sheet after removal from the film to be attached to other locations upon a patient or other object.

9. The surgical drape of claim 4 further comprising surgical attachments positioned upon the sheet material.

10. The surgical drape of claim 9 wherein the attachment is a pouch.

11. The surgical drape of claim 1 wherein the drape has been treated to substantially prevent edge adhesion in the rolled configuration.

12. The surgical drape of claim 11 wherein edge adhesion is substantially prevented by application of strips at the outer edges of the drape.

13. The surgical drape of claim 12 wherein the strips comprise polyolefin films.

14. The surgical drape of claim 12 wherein the strips comprise non-woven sheets.

15. The surgical drape of claim 12 wherein the core extends sufficiently beyond the adhesive coated drape to function as application handles.

16. The surgical drape of claim 15 wherein the core is comprised of cylindrical plastic or cardboard.

17. The surgical drape of claim 12 wherein said strips are relatively non-extensible to substantially reduce unwanted extension of the drape during unrolling thereof.

18. The surgical drape of claim 11 wherein edge adhesion is substantially prevented by application of a particulate material to the outer edges of the drape.

19. The surgical drape of claim 11 wherein edge adhesion is substantially prevented by leaving zones of non-adhesive coated film at the outer edges of the drape.

20. The surgical drape of claim 11 wherein the core extends sufficiently beyond the adhesive coated drape to function as application handles.

21. The surgical drape of claim 20 wherein the core is comprised of cylindrical plastic or cardboard.

22. The surgical drape of claim 11 wherein a relatively stiff handle portion extends from the end opposite the core.

23. The surgical drape of claim 1 wherein the drape is rolled pressure sensitive adhesive inward around the core.

24. The surgical drape of claim 1 wherein the drape is rolled pressure sensitive adhesive outward around the core.

* * * * *